(12) United States Patent
Plata-Salaman et al.

(10) Patent No.: US 6,908,902 B2
(45) Date of Patent: Jun. 21, 2005

(54) TREATMENT OF NEUROLOGICAL DYSFUNCTION COMPRISING FRUCTOPYRANOSE SULFAMATES AND ERYTHROPOIETIN

(75) Inventors: Carlos Plata-Salaman, Ambler, PA (US); Virginia Smith-Swintosky, Hatfield, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/056,828

(22) Filed: Jan. 24, 2002

(65) Prior Publication Data

US 2002/0169109 A1 Nov. 14, 2002

Related U.S. Application Data

(60) Provisional application No. 60/266,194, filed on Feb. 2, 2001.

(51) Int. Cl.$^7$ .................. A61K 31/00; A61K 31/70; A01N 43/04
(52) U.S. Cl. .................. 514/23; 514/451; 514/453; 514/454; 514/12
(58) Field of Search .................. 514/23, 451; 424/9.34

(56) References Cited

U.S. PATENT DOCUMENTS

| | | | |
|---|---|---|---|
| 4,513,006 | A | 4/1985 | Maryanoff et al. |
| 4,703,008 | A | 10/1987 | Lin |
| 5,242,942 | A | 9/1993 | Costanzo et al. |
| 5,354,934 | A | 10/1994 | Pitt et al. |
| 5,384,327 | A | 1/1995 | Costanzo et al. |
| 5,571,787 | A | 11/1996 | O'Brien |
| 5,643,575 | A | 7/1997 | Martinez et al. |
| 5,688,679 | A | 11/1997 | Powell |
| 5,696,080 | A | 12/1997 | O'Brien et al. |
| 5,700,909 | A | 12/1997 | O'Brien |
| 5,714,459 | A | 2/1998 | O'Brien |
| 5,753,694 | A | 5/1998 | Shank |
| 5,767,078 | A | 6/1998 | Johnson et al. |
| 5,773,569 | A | 6/1998 | Wrighton et al. |
| 6,001,800 | A | 12/1999 | Mehta et al. |

FOREIGN PATENT DOCUMENTS

| | | |
|---|---|---|
| EP | 640619 | 3/1995 |
| WO | WO 94/12650 | 6/1994 |
| WO | WO 95/03034 | 2/1995 |
| WO | WO 96/40772 | 12/1996 |
| WO | WO 98/00124 | 1/1998 |
| WO | WO 98/05363 | 2/1998 |
| WO | WO 99/05268 | 2/1999 |
| WO | WO 99/11781 | 3/1999 |
| WO | WO 99/21966 | 5/1999 |
| WO | WO 99/38890 | 8/1999 |
| WO | WO 99/66054 | 12/1999 |
| WO | WO 00/61138 | 10/2000 |
| WO | WO 00/61138 A1 * | 10/2000 |
| WO | WO 00/61164 * | 10/2000 |

OTHER PUBLICATIONS

Temple et al., Recombinant erythropoietin improves cognitive function in patients maintained on chronic ambulatory peritoneal dialysis, Nephrol Dial Transplant (1995) 10:1733–1738.*

Sachdeo, Rajesh C., Topiramate: Clinical Profile in Epilepsy, Clin Pharmacokinet, May 1998, 34(5):335–346.*

NINDS Traumatic Brain Injury Information Page: http://www.ninds.nih.gov/health_and_medical /disorders/tbi_doc.htm; Jul. 1, 2001.*

Maryanoff et al., Structure–Activity Studies on Anticonvulsant Sugar Sulfamates Related to Topiramate. Enhanced Potency with Cyclic Sulfamate Derivatives, J. Med. Chem., 1998, vol. 41, pp. 1315–1343.*

NINDS Alzheimer's Disease Information Page: http://www.ninds.nih.gov/health_and_medical/disorders/alzheimersdisease_doc.htm; Sep. 10, 2003.*

NINDS Epliepsy Information Page: http://www.ninds.nih.gov/health_and_medical/disorders/epilepsy.htm; Jul. 1, 2001.*

NINDS Multiple Sclerosis Information Page: http://www.ninds.nih.gov/health_and_medical/disorders/epilepsy.htm; Jul. 1, 2001.*

Alafaci et al., "Effect of Recombinant Human Erythropoietin on Cerebral Ischemia Following Experimental Subarachnoid Hemorrhage", *Eur. J. Pharmacol.* (2000) 406(2):219–225.

Aldenkamp et al., "A Multicenter, Randomized Clinical Study to Evaluate the Effect on Cognitive Function of Topiramate Compared with Valproate as Add–On Therapy to Carbamazepine in Patients with Partial–Onset Seizures", *Epilepsia* (2000) 41(9):1167–1178.

William M. Armstead, "Age–Dependent Cerebral Hemodynamic Effects of Traumatic Brain Injury in Newborn and Juvenile Pigs", *Microcirculation* (2000) 7(4):225–235.

D. M. Basso, "Neuroanatomical Substrates of Functional Recovery after Experimental Spinal Cord Injury: Implications of Basic Science Research for Human Spinal Cord Injury", *Phys. Ther.* (2000) 80(8):808–817.

Bernaudin et al., "A Potential Role for Erythropoietin in Focal Permanent Cerebral Ischemia in Mice", *J. Cereb. Blood Flow Metab.* (1999) 19(6):643–651.

Robert F. Brady, "Cyclic Acetals of Ketoses, Part III: Re–Investigation of the Synthesis of the Isomeric $^{DI}$–O–isopropylidene–$^{\beta-D}$–Fructopyranoses", *Carbohydrate Res.* (1970) 15(1):35–40.

(Continued)

*Primary Examiner*—James O. Wilson
*Assistant Examiner*—Traviss C. McIntosh, III
(74) *Attorney, Agent, or Firm*—Woodcock Washburn LLP

(57) ABSTRACT

Co-therapy for the treatment of neurological dysfunctions comprising administration of one or more fructopyranose sulfamates and erythropoietin.

7 Claims, No Drawings

OTHER PUBLICATIONS

Brines et al., "Erythropoietin Crosses the Blood–Brain Barrier to Protect Against Experimental Brain Injury", *P. N. A. S. U S A* (2000) 97(19):10526–10531.

Leslie A. Burton and Cynthia Harden, "Effect of Topiramate on Attention", *Epilepsy Res.* (1997) 27(1):29–32.

Campana et al., "Identification of a Neurotrophic Sequence of Erythropoietin", *Inter. J. Mol. Med.* (1998) 1(1):235–241.

Di Giulio et al., "Glycosaminoglycans Co–Administration Enhance Insulin–Like Growth Factor–I Neuroprotective and Neuroregenerative Activity in Traumatic and Genetic Models of Motor Neuron Disease: A Review", *Int. J. Dev. Neurosci.* (2000) 18(4–5):339–346.

Faught et al., "Topiramite Dose–Ranging Trial in Refractory Partial Epilepsy", *Epilepsia* (1995) 36(S4): p. 33.

Tracy A. Glauser, "Video Atlas of Epileptic Seizures: Classical Examples", *Epilepsia* (1999) 40(S5):S71–80. vol. 40(5) pp. 664–5.

Greco et al., "The Search for Synergy: A Critical Review from a Response Surface Perspective", *Pharmacol. Rev.* (1995) 47(2):331–385.

Byung H. Han and David M. Holtzman, "BDNF Protects the Neonatal Brain from Hypoxic–Ischemic Injury In Vivo via the ERK Pathway", *J. Neurosci.* (2000) 20(15):5775–5781.

Mir Hedayatullah and Alain Guy, "Synthesis and Reduction of Aryl Azidosulfates (Synthese et Reduction d'Azidosulfates d'Aryle)", *Tetrahedron Lett.* (1975), 16(29):2455–2458.

Herbert O. House, "Metal Hydride Reductions and Related Reductions", *Modern Synthetic Reactions* (Organic Chemistry Monograph Series), $2^{nd}$ Ed. (Benjamin–Cummings Publishing Co., Menlo Park, CA 1972) pp. 45–144.

Juul et al., "Immunohistochemical Localization of Erythropoietin and its Receptors in the Developing Human Brain", *Pediatr. Dev. Pathol.* (1999) 2(2):148–158.

Juul et al., Erythropoietin and Erythropoietin Receptor in the Developing Human Central Nervous System, *Pediatr. Res.* (1998) 43(1):43(1):40–49.

Juul et al., "Erythropoietin in the Cerebrospinal Fluid of Neonates who Sustained CNS Injury", *Pediatr. Res.* (1999) 46(5):543–547.

L. Kambova, "Recombination Erythropoietin Improves Cognitive Function in Chronic Haemodialysis Patients", *Nephrol. Dial. Transplant.* (1998) 13(1):229.

Koshimura et al., "Effects of Erythropoietin on Neuronal Activity", *J. Neurochem.* (1999) 72(6):2565–2572.

Sanford B. Krantz, "Erythropoietin", *Blood* (1991) 77(3): 419–434.

Gerald L. Larson and Antonio Hernandez, "Reaction of Trimethylsilyl Enol Ethers with Diols", *J. Org. Chem.* (1973) 38(22):3935–3936.

H. L. Laurer and T. K. McIntosh, "Experimental Models of Brain Trauma", *Curr. Opin. Neurol.* (1999) 12(6):715–721.

Lee et al., "Protective Effect of Topiramate Against Hippocampal Neuronal Damage after Global Ischemia in the Gerbils", *Neuroscience Letters* (2000) 281(2–3):183–186.

Maryanoff et al., "Anticonvulsant O–Alkyl Sulfamates: 2,3:4, 5–Bis–O–(1–Methylethylidene)–Beta–D–Fructopyranose Sulfamate and Related Compounds", *J. Medicinal Chemistry* (1987) 30(5):880–887.

Maryanoff et al., "Anticonvulsant Sugar Sulfamates: Potent Cyclic Sulfate and Cyclic Sulfite Analogues of Topiramate", *Bioorg. Med. Chem. Lett.* (1993) 3(12):2653–2656.

Maryanoff et al., "Structure—Activity Studies on Anticonvulsant Sugar Sulfamates Related to Topiramate: Enhanced Potency with Cyclic Sulfate Derivatives", *J. Med. Chem.* (1998) 41(8):1315–1343.

M. Mason–Garcia and B. S. Beckman, "Signal Transduction in Erythropiesis", *Faseb Journal* (1991) 5(14): 2958–2964.

Mattson et al., "Calcium, Free Radicals and Excitotoxic Neuronal Death in Primary Cell Culture", *Methods Cell Biol.* (1994) 46:187–216.

Italo Mocchetti and Jean R. Wrathall, "Neurotropic Factors In Central Nervous System Trauma", *J. Neurotrauma* (1995) 12(5):853–870.

Morishita et al., "Erythropoietin Receptor is Expressed in Rat Hippocampal and Cerebral Cortical Neurons, and Erythropoietin Prevent In Vitro Glutamate–Induced Neuronal Death", *Neuroscience* (1997) 76(1):105–116.

Nakamura et al., "Inhibition by Topiramate of Seizures in Spontaneously Epileptic Rats and DBA/2 Mice", *Eur. J. Pharmacol.* (1994) 254(1–2):83–89.

Newey et al., "Alternative Splicing of Dystrobrevin Regulates the Stoichiometry of Syntrophin Binding to the Dystrophin Protein Complex", *Curr. Biol.* (2000) 10(20):1295–1298.

A. R. Nissenson, "Eptoein And Cognitive Function", *Am. J. Kidney Dis.* (1992) 20(1S1)21–24.

Raghupathi et al., "Apoptosis After Traumatic Brain Injury", *J. Neurotrauma* (2000) 17(10):927–938.

Heikki Rauvala and H. Benjamin Peng, "HB–GAM (Heparin–Binding Growth–Associated Molecule) and Heparin–Type Glycans in the Development and Plasticity of Neuron–Target Contacts", *Prog. Neurobiol.* (1997) 52(2):127–144.

Reife et al., "Topiramate as Add–On Therapy: Pooled Anlaysis of Randomized Controlled Trials in Adults", *Epilepsia* (2000) 41(S1):S66–71.

Ronn et al., "The Neural Cell Adhesion Molecule in Synaptic Plasticity and Ageing", *Int. J. Dev. Neurosci.* (2000) 18(2–3):193–199.

Sachdeo et al., "Topiramate: Double–Blind Trial as Monotherapy", *Epilepsia* (1995) 36(S4):p. 33.

Rajesh C. Sachdeo, "Topiramate: Clinical Profile in Epilepsy", *Clin. Pharmacokinet.* (1998) 34(5):335–346.

Sadamoto et al., "Erythropoietin Prevent Place Navigation Disability and Cortical Infarction in Rats with Permanent Occulsion of the Middle Cerebral Artery", *Biochem. Biophys. Res. Comm.* (1998) 9; 253(1):26–32.

Sakanaka et al., "In Vivo Evidence that Erthropoietin Protects Neurons from Ischemic Damage", *P.N.A.S. USA* (1998) 95(8):4635–4640.

Martin E. Schwab, "Experimental Aspects of Spinal Cord Regeneration", *Curr. Opin. Neurol. Neurosurg.* (1993) 6(4):549–553.

Irina Semkova and Josef Krieglstein, "Neuroprotection Mediated via Neurotrophic Factors and Induction of Neurotrophic Factors", *Brain Res. Rev.* (1999) 30(2):176–188.

Shank et al., "Topiramate: Preclinical Evaluation of a Structurally Novel Anticonvulsant", *Epilepsia* (1994) 35(2):450–460.

Amy D. Sinor and David A. Greenberg, "Erythropoietin Protects Cultured Cortical Neurons, but not Astroglia, from Hypoxia and AMPA Toxicity", *Neurosci. Lett.* (2000) 290(3):213–215.

Smith–Swintosky et al., "Topiramate Promotes Neurite Outgrowth and Recovery of Function After Nerve Injury", *NeuroReport* (2001) 12(5):1031–1034.

Tabira et al., "Neurotrophic Effect of Hematopoietic Cytokines on Cholinergic and Other Neurons In Vitro", *Int. J. Dev. Neurosci.* (1995) 13(3/4):241–252.

Yuji Taoka and Kenji Okajima, "Spinal Cord Injury in the Rat", *Prog. Neurobiol.* (1998) 56(3):341–358.

Temple et al., "Recombinant Erythropoietin Improves Cognitive Function in Patients Maintained on Chronic Ambulatory Peritoneal Dialysis", *Nephrol. Dial. Transplant.* (1995) 10(9):1733–1738.

Thompson et al., Effects of Topiramate on Cognitive Function, *J. Neurol. Neurosurg. Psych.* (2000) 69(5):636–641.

Tsuchiya et al., "3–Deoxygenation of Methyl α–D–Glucopyranosides by Treatment of Their 3–$^{O,N,N}$–Dimethylsulfamoyl) Derivatives with Sodium Metal in Liquid Ammonia", *Tethrahedron Lett.* (1978) 19(36):3365–3368.

Verderio et al., "Synaptogenesis in Hippocampal Cultures", *Cell. Mol. Life Sci.* (1999) 55(11):1148–1462.

C. S. von Bartheld, "Neurotrophins in the Developing and Regenerating Visual System", *Histol. Histopathol.* (1998) 13(2):437–459.

Albert Wauquier and Zhou Shangdan, "Topiramate: A Potent Anticonvulsant in the Amygdala–Kindled Rat", *Epilepsy Research* (1996) 24(2):73–77.

Yang, et al., "Enhanced Neuroprotection and Reduced Hemorrhagic Incidence in Focal Cerebral Ischemia of Rat by Low Dose Combination Therapy of Urokinase and Topiramate", *Neuropharmacol.* (2000) 39(5):881–888.

Yang et al., "Neuroprotection by Delayed Administration of Topiramate in a Rat Model of Middle Cerebral Artery Embolization", *Brain Res.* (1998) 804(2):169–176.

Yang et al., "Usefulness of Postischemic Thrombolysis With or Without Neuroprotection in a Focal Embolic Model of Cerebral Ischemia", *J. Neurosurg.* (2000) 92(5):841–847.

Zhang et al., "Topical Application of Neurotrophin–3 Attenuates Ischemic Brain Injury after Transient Middle Cerebral Artery Occlusion in Rats", *Brain Res.* (1999) 842(1):211–214.

\* cited by examiner

TREATMENT OF NEUROLOGICAL DYSFUNCTION COMPRISING FRUCTOPYRANOSE SULFAMATES AND ERYTHROPOIETIN

CROSS REFERENCE TO RELATED APPLICATION

This application claims priority from U.S. provisional application Ser. No. 60/226,194, filed Feb. 2, 2001, the contents of which are hereby incorporated by reference.

BACKGROUND OF THE INVENTION

Fructopyranose sulfamates, compounds of Formula I,

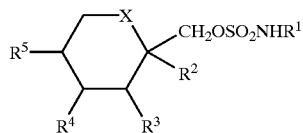

are structurally novel anti-epileptic compounds that are highly effective anticonvulsants in animal tests (Maryanoff et al., *J. Med. Chem.* (1987) 30:880–887; Maryanoff et al., *Bioorg. Med. Chem. Lett.* (1993) 3:2653–2656; Shank et al., *Epilepsia* (1994) 35:450–460; and Maryanoff et al., *J. Med. Chem.* (1998) 41:1315–1343). These compounds are covered by three U.S. Patents: U.S. Pat. No. 4,513,006, U.S. Pat. No. 5,242,942, and U.S. Pat. No. 5,384,327. One of these compounds, 2,3:4,5-bis-O-(1-methylethylidene)-β-D-fructopyranose sulfamate known as topiramate, has been demonstrated in clinical trials of human epilepsy to be effective as adjunctive therapy or as monotherapy in treating simple and complex partial seizures and secondarily generalized seizures (Faught et al., *Epilepsia* (1995) 36(S4):33; Sachdeo et al., *Epilepsia* (1995) 36(S4):33; T. A. Glauser, *Epilepsia* (1999) 40(S5):S71–80; and R. C. Sachdeo, *Clin. Pharmacokinet.* (1998) 34:335–346), and is currently marketed for the treatment of seizures in patients with simple and complex partial epilepsy and seizures in patients with primary or secondary generalized seizures in the United States, Europe and most other markets throughout the world.

Fructopyranose sulfamates, compounds of Formula I, were initially found to possess anticonvulsant activity in the traditional maximal electroshock seizure (MES) test in mice (Shank et al., *Epilepsia* (1994) 35:450–460). Subsequent studies revealed that Compounds of Formula I were also highly effective in the MES test in rats. Topiramate was also found to effectively block seizures in several rodent models of epilepsy (Nakamura et al., *Eur. J. Pharmacol.* (1994) 254:83–89), and in an animal model of kindled epilepsy (A. Wauquier and S. Zhou, *Epilepsy Res.* (1996) 24:73–77).

Shank et al., in WIPO publication WO 98/00124, disclose the use of fructopyranose sulfamates, compounds of formula I, for the treatment of postischemic neurodegeneration. Further, it has been reported that topiramate has a dose- and use-dependent neuroprotective effect, when used two hours after MCA embolization in a rat model of focal ischemia (Yang et al., *Brain Res.* (1998) 804(2):169–76). The neuroprotective effect of topiramate against neuronal damage following global ischemia in gerbils via bilateral carotid occlusion and in rats by cardiac arrest has also been described (Lee et al., *Neuroscience Let.* (2000) 281(2–3):183–186; Edmonds et al., *Life Sciences* (2001) 69:2265–2277).

More recently, the addition of topiramate to low dose urokinase was suggested to benefit ischemic stroke treatment by improving neurological recovery, attenuating infarction size, and reducing the risk of cerebral damage (Yang et al., *Neuropharm.* (2000) 39(5):881–888; Yang et al., *J. Neurosurg.* (2000) 92(5):841–847).

R. P. Shank, in WIPO publication WO 00/61138, discloses the use of fructopyranose sulfamates, compounds of formula I, for the treatment of chronic neurodegenerative disorders. R. P. Shank, in U.S. Pat. No. 5,753,694, discloses the use of fructopyranose sulfamates, compounds of formula I, for the treatment of amyotrophic lateral sclerosis (ALS).

Recent studies showed that topiramate promotes neurite outgrowth in rat neuronal cultures and recovery of function after facial nerve crush injury in the rat. In these studies, topiramate's neurotrophic effects were dose-dependent (Smith-Swintosky et al., *NeuroReport* (2001) 17:1031–1034).

There is some suggestion that topiramate may impair attention in some individuals, a frequently noted side effect of anti-epileptic (L. A. Burton and C. Harden, *Epilepsy Res.* (1997) 27:29–32). It has also been reported that topiramate, under certain circumstances, may have a negative impact on cognition, consistent with subjective complaints of some patients (Thompson et al., *J. Neuro. Neurosurg. Psych.* (2000) 69(5):636–641). However, these central nervous system effects of topiramate are generally mild to moderate in severity, usually occur early in treatment (often during titration), resolve with continued treatment and are reversible (Reife et al., *Epilepsia* (2000) 41(Supp 1):S66–S71). Additionally, the gradual introduction of topiramate reduces the extent of cognitive impairment (Aldenkamp et al., *Epilepsia* (2000) 41(9):1167–1178).

Erythropoietin (EPO) is a glycoprotein hormone produced by the kidney in response to tissue hypoxia that stimulates red blood cell production in the bone marrow. The gene for erythropoietin has been cloned and expressed in Chinese hamster ovary (CHO) cells as described in U.S. Pat. No. 4,703,008. Recombinant human erythropoietin (r-HuEPO, rhEPO, Epoetin alfa) has an amino acid sequence identical to that of human urinary erythropoietin, and the two are indistinguishable in chemical, physical and immunological tests. Recombinant human erythropoietin acts by increasing the number of cells capable of differentiating into mature erythrocytes, triggering their differentiation and augmenting hemoglobin synthesis in developing erythroblasts (S. B. Krantz, *Blood* (1991) 77:419–434; B. S. Beckman and M. Mason-Garcia, *Faseb Journal* (1991) 5:2958–2964).

Epoetin alfa is approved for sale in many countries for the treatment of anemia. Epoetin alfa has other potential uses, which include, but are not limited to anemia in chronic renal failure (dialysis and pre-dialysis), anemia in zidovudine treated HIV positive patients, anemia in cancer patients receiving platinum-based chemotherapy, as a facilitator of autologous blood pre-donation, and as a peri-surgical adjuvant to reduce the likelihood of requiring allogeneic blood transfusions in patients undergoing orthopedic surgery.

EPO influences neuronal stem cells, likely during embryonic development, and possibly during in vitro experiments of differentiation (Juul et al., *Pediatr. Dev. Pathol.* (1999) 2(2):148–158; Juul et al., *Pediatr. Res.* (1998) 43(1):40–49). Further, neonates and infants that suffer CNS injury via hypoxia, meningitis, and intraventricular hemorrhage, show an EPO induced neuroprotective effect (Juul et al., *Ped. Res.* (1999) 46(5):543–547).

EPO helps prevent apoptosis of neural tissue in cases of insult that create hypoxia. This may de due to the local production of EPO by astrocytes and other brain cells (Morishita et al., *Neuroscience* (1996) 76(1):105–116). In addition, EPO could cross the blood-brain barrier in clinical conditions associated with a disruption, breakdown, or dysregulation of the barrier. Neuroprotection has been demonstrated in gerbil hippocampal and rat cerebrocortical tissue (Sakanaka et al., *P.N.A.S. USA* (1998) 95(8):4635–4640; Sadamoto et al., *Biochem. Biophys. Res. Commun.* (1998) 253(1):26–32).

EPO administration reduces brain infarct volume in mice subjected to cerebral ischemia (Bernaudin et al., *J. Cereb. Blood Flow Metab.* (1999) 19(6):643–51), reduces brain infarct volume in rats after middle cerebral artery occlusion (Brines et al., *P.N.A.S. USA* (2000) 97(19):10526–31), prevents place navigation disability and cortical infarction in rats with permanent occlusion of the middle cerebral (Sadamoto et al., *Biochem. Biophys. Res. Commun.* (1998) 9/253(1):26–32), reduces cortical necrotic neuron count in a rabbit model of cerebral ischemia following subarachnoid hemorrhage (Alafaci et al., *Eur. J. Pharmacol.* (2000) 13/406(2):219–25), and protects cortical neurons from hypoxia and AMPA toxicity (A. D. Sinor and D. A. Greenberg, *Neurosci. Lett.* (2000) 290(3):213–5). EPO also improves cognitive function in chronic hemodialysis patients (L. Kambova, *Nephrol. Dial. Transplant.* (1998) 13(1):229–30; Temple et al., *Nephrol. Dial. Transplant.* (1995) 10(9):1733–1738; and A. R. Nissenson, *Am. J. Kidney Dis.* (1992) 20(1 Supp. 1):21–24).

EPO also induces biological effects on PC12 cells including change in $Ca^{+2}$, change in membrane potential, and promotion of survival after glutamate toxicity and NGF withdrawal. This has been interpreted as EPO stimulating neural function and viability (Koshimura et al., *J. Neurochem.* (1999) 72(6):2565–2572; Tabira et al., *Int. Dev. Neurosci.* (1995) 13(3/4):241–252).

EPO may also influence neuronal stem cell commitment to drive differentiation of neurons as opposed to astrocytes or oligodendrocytes. This is similar to activity of EPO, where it functions to drive commitment of hematopoietic stem cells to produce red blood cells (RBCs). CNS hypoxic injury, results in the production of EPO from astrocytes which commits neuronal stem cells to differentiate into neurons, and which exhibits a neuroprotective function for existing neurons (WIPO publication number WO 99/21966, published on May 6, 1999 by Weiss et al.).

More recently, Ehrenreich et al., in WIPO publication WO 00/35475, describe the use of erythropoietin for the treatment of cerebral ischemia, for example in stroke patients.

Brines et al., in WIPO publication WO 00/61164, describe modulation of excitable tissue function by peripheral administration of erythropoietin.

O'Brien et al., in U.S. Pat. No. 5,700,909, issued Dec. 23, 1997 (Seq. ID. No. 11), disclose a 17 amino acid peptide sequence of EPO which acts through the EPO-R to induce biological activity in NS20Y, SK-N-MC, and PC12 cells including sprouting, differentiation, neuroprotection, and prevention of neuronal cell death. This peptide (designed epopeptide AB) does not promote proliferation of hematologic cells, thus it appears inactive in erythropoietic cell lines well understood for their EPO responsiveness. When epopeptide AB was injected into the muscle of mice, the frequency of motor end plate sprouting in the adjacent muscles increased in a manner similar to that induced by ciliary neurotrophic factor. These data are interpreted within the concept that neuronal (but not hematological) cells respond to a peptide sequence within EPO and that EPO may have separate domains for neurotrophic and hematotrophic activity (Campana et al., *Int. J. Mol. Med.* (1998) 1(1):235–241; J. S. O'Brien in U.S. Pat. No. 5,700,909, issued Dec. 23, 1997; J. S. O'Brien in U.S. Pat. No. 5,571,787, issued Nov. 5, 1996; J. S. O'Brien in U.S. Pat. No. 5,714,459, issued Feb. 3, 1998; and J. S. O'Brien and Y. Kashimoto in U.S. Pat. No. 5,696,080, issued Dec. 9, 1997).

Zivin et al., in WIPO publication WO 96/40772, disclose peptide dimers which behave as cell surface receptor agonists in their dimeric form, including for example, peptide dimers that bind to the erythropoietin receptor and simulate its function.

Co-therapy using fructopyranose sulfamates and erythropoietin has not, however, yet been contemplated in the art.

SUMMARY OF THE INVENTION

It has now been found that co-therapy with one or more fructopyranose sulfamates and erythropoietin is useful in treating neurological dysfunction.

Illustrative of the invention is co-therapy, to a subject in need thereof, of one or more fructopyranose sulfamates and erythropoietin for the treatment of a neurological dysfunction, wherein the fructopyranose sulfamate(s) and the erythropoietin may be administered by any suitable means, simultaneously, sequentially, separately or in a single pharmaceutical composition.

Illustrative of the invention is a pharmaceutical composition comprising a pharmaceutically acceptable carrier, one or more fructopyranose sulfamates and erythropoietin. An illustration of the invention is a pharmaceutical composition made by mixing one or more fructopyranose sulfamates, erythropoietin and a pharmaceutically acceptable carrier. Illustrating the invention is a process for making a pharmaceutical composition comprising mixing one or more fructopyranose sulfamates, erythropoietin and a pharmaceutically acceptable carrier.

Also included in the present invention is the use of one or more fructopyranose sulfamates and erythropoietin in the preparation of a medicament for treating: (a) an acute neurodegenerative disorder, (b) a chronic neurodegenerative disorder, (c) dementia, (d) memory loss, (e) diminished mental capacity, (f) mental deterioration, (g) a neurological manifestation resulting from disease or injury of any physiological system, (h) a psychiatric manifestation resulting from disease or injury of any physiological system, (i) a neurological manifestation of peripheral diseases, () a psychiatric manifestation of peripheral diseases, (k) a neurological manifestation resulting from an epileptic condition, (l) a psychiatric manifestation resulting from an epileptic conditions, (m) a neurological manifestation of a post-ictal, post-seizure or inter-ictal state and (n) a psychiatric manifestation of a post-ictal, post-seizure or inter-ictal state, in a subject in need thereof.

Also included in the present invention is the use of topiramate and erythropoietin in the preparation of a medicament for treating: (a) an acute neurodegenerative disorder, (b) a chronic neurodegenerative disorder, (c) dementia, (d) memory loss, (e) diminished mental capacity, (f) mental deterioration, (g) a neurological manifestation resulting from disease or injury of any physiological system, (h) a psychiatric manifestation resulting from disease or injury of any physiological system, (i) a neurological manifestation of peripheral diseases, j) a psychiatric manifestation of peripheral diseases, (k) a neurological manifestation resulting from an epileptic condition, (l) a psychiatric manifestation resulting from an epileptic conditions, (m) a neurological manifestation of a post-ictal, post-seizure or inter-ictal state and (n) a psychiatric manifestation of a post-ictal, post-seizure or inter-ictal state, in a subject in need thereof.

DETAILED DESCRIPTION

The present invention provides a method for treatment of neurological dysfunction comprising administration of one or more fructopyranose sulfamates and administration of erythropoietin (EPO), wherein the amount of the fructopyranose sulfamate(s) and the amount of the erythropoietin are selected to produce a synergistic effect.

In an embodiment of the present invention, the fructopyranose sulfamate is topiramate. In another embodiment of the present invention, the erythropoietin is epoetin alfa. In yet another embodiment of the present invention, the fructopyranose sulfamate is topiramate and the erythropoietin is epoetin alfa.

Also included in the present invention is a pharmaceutical composition comprising one or more fructopyranose sulfamates and erythropoietin. Also included in the present invention is a pharmaceutical composition comprising topiramate and erythropoietin.

As used herein, the term "co-therapy" shall mean treatment of a subject in need thereof, with administration of one or more fructopyranose sulfamates and administration of erythropoietin, wherein the fructopyranose sulfamate(s) and the erythropoietin are administered by any suitable means, simultaneously, sequentially, separately or in a single pharmaceutical formulation. Where the fructopyranose sulfamate(s) and the erythropoietin are administered in separate dosage forms, the number of dosages administered for each compound may be the same or different. The fructopyranose sulfamate(s) and the erythropoietin may be administered via the same or different routes of administration. The fructopyranose sulfamate(s) and the erythropoietin may be administered according to simultaneous or alternating regimens, at the same or different times during the course of the therapy, concurrently in divided or single forms.

As used herein, the term "neurological dysfunction" shall include acute neurodegenerative disorders; chronic neurodegenerative disorders; dementia, regardless of underlying etiology; neurological and psychiatric manifestations resulting from disease or injury of any physiological system; neurological and psychiatric manifestations of peripheral diseases; neurological and psychiatric manifestations of an epileptic condition, a post-ictal, post-seizure or inter-ictal state; memory loss; diminished mental capacity and mental deterioration.

As used herein, the term "psychiatric manifestations" shall include psychiatric and neuropsychiatric manifestations of any disease or injury. Suitable examples include, but are not limited to, depression, anxiety, irritability, euphoria, aggressiveness, apathy, psychosis, delusions, hallucinations, dysphoria, agitation, aberrant behavior and disturbances during daytime or nighttime, eating abnormalities, anorexia.

Acute neurodegenerative disorders included within the methods of the present invention include, but are not limited, to various types of acute neurodegenerative disorders associated with neuronal cell death or compromise including cerebrovascular insufficiency, focal brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome.

Chronic neurodegenerative disorders included within the methods of the present invention included, but are not limited to, Alzheimer's disease, Pick's disease, diffuse Lewy body disease, progressive supranuclear palsy (Steel-Richardson syndrome), multi-system degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/ spinocerebellar ataxia type 3 and olivopontocerebellar degenerations, Gilles De La Tourette's disease, bulbar and pseudobulbar palsy, spinal and spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multi-focal leukoencephalopathy, familial dysautonomia (Riley-Day syndrome), and prion diseases (including, but not limited to, Creutzfeldt-Jakob, Gerstmann-Sträussler-Scheinker disease, Kuru and fatal familial insomnia).

Other conditions included within the methods of the present invention include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia.

Also included within the present invention are the treatment and/or prevention of memory disorders, including but not limited to, memory loss, diminished mental capacity and mental deterioration.

Also included within the present invention are the treatment and/or prevention of neurological and psychiatric manifestations resulting from chemical, toxic, infectious and radiation injury of the nervous system and as a result of prematurity; treatment and/or prevention of neurological and psychiatric consequences of encephalopathies including, but not limited to, those of anoxic-ischemia, hepatic, glycemic, uremic, electrolyte and endocrine origin; the treatment and/or prevention of neurological (including, but not limited to, cognitive) and psychiatric (including, but not limited to, psychopathology, depression, or anxiety), manifestations associated with peripheral diseases; and the treatment and/or prevention of plexopathies (including plexus palsies), multifocal neuropathies, sensory neuropathies, motor neuropathies, sensory-motor neuropathies, infections neuropathies, autonomic neuropathies, sensory-autonomic neuropathies, demyelinating neuropathies (including, but not limited to, Guillain-Barre syndrome and chronic inflammatory demyelinating polyradiculoneuropathy), other inflammatory and immune neuropathies, neuropathies induced by drugs, neuropathies induced by pharmacological treatments, neuropathies induced by toxins, traumatic neuropathies (including, but not limited to, compression, crush, laceration and segmentation neuropathies), metabolic neuropathies, endocrine and paraneoplastic neuropathies, and other neuropathies such as Charcot-Marie-Tooth disease (type 1a, 1b, 2, 4a,1-X linked), Friedreich's ataxia, metachromatic leukodystrophy, Refsum's disease, adrenomyeloneuropathy, Ataxia-telangiectasia, Déjerine-Sottas neuropathy (types A and B), Lambert-Eaton syndrome, and disorders of the cranial nerves.

Also included within the present invention are the treatment and/or prevention of neurological and psychiatric manifestations resulting from disease or injury of any physiological system.

Also included within the present invention are the treatment and/or prevention of neurological and psychiatric manifestations resulting from acute neurodegenerative disorders (including, but not limited to, cerebrovascular insufficiency, focal brain trauma, diffuse brain damage, and spinal cord injury), such as depression, anxiety disorders, psychopathology, cognitive deficits, memory loss and diminished mental capacity.

Also included within the present invention are the treatment and/or prevention of neurological and psychiatric manifestations resulting from any epileptic condition, including the neurological and psychiatric manifestations resulting from post-seizure or post-ictal states, such as psychosis, depression, anxiety disorders, cognitive deficits, memory loss, or neurological and psychiatric manifestations that can occur inter-ictally such as psychosis.

Other clinical conditions included within the methods of the present invention include treating and/or preventing the neurological (including, but not limited to, cognitive) and psychiatric (including, but not limited to, psychopathology, depression, or anxiety), manifestations associated with peripheral diseases including, but not limited to, EPO deficiency (e.g., renal disease), blood loss of any kind (including, but not limited to, hemodialysis, peritoneal dialysis, diagnostic sampling, occult gastrointestinal bleeding), renal failure and end-stage renal disease, renal transplantation, and other conditions associated with anemia, and neurological and psychiatric manifestations, including but not limited to, hematological and non-hematological malignancies/cancer, patients receiving chemotherapy (including, but not limited to, cisplatin) and other drugs (including, but not limited to, zidovudine), other hematological disorders (including, but not limited to, sickle cell anemia and thalassemia), inflammatory and infectious disorders (including, but not limited to, human immunodeficiency infections), chronic systemic autoimmune diseases (including, but not limited to, systemic lupus erythematosus), Henoch Schonlein Purpura, and hemolytic uremic syndrome.

The invention includes, but is not limited to, a method of treating and/or preventing acute neurodegenerative disorders including, but not limited to, cerebrovascular insufficiency, focal brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), which method comprises co-therapy, to a subject in need thereof of, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing chronic neurodegenerative disorders including, but not limited to, Alzheimer's disease, Pick's disease, diffuse Lewy body disease, progressive supranuclear palsy (Steel-Richardson syndrome), multi-system degeneration (Shy-Drager syndrome), chronic epileptic conditions associated with neurodegeneration, motor neuron diseases, amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 degeneration, olivopontocerebellar degeneration, Gilles De La Tourette's disease, bulbar palsy, pseudobulbar palsy, spinal muscular atrophy, spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), prion disease, Creutzfeldt-Jakob disease, Gerstmann-Sträussler-Scheinker disease, Kuru insomnia and fatal familial insomnia, which method comprises co-therapy, to a subject in need thereof of, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing clinical manifestations of Alzheimer's disease that include, but are not limited to, cognitive and language deficits, apraxias, depression, delusions and other psychiatric symptoms and signs, and movement and gait abnormalities, which method comprises co-therapy, to a subject in need thereof of, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing dementia, including dementia in Alzheimer's disease (as well as a method for treating and/or preventing other clinical manifestations of Alzheimer's disease that include, but are not limited to, cognitive and language deficits, apraxias, depression, delusions and other psychiatric symptoms and signs, and movement and gait abnormalities) which method comprises co-therapy, to a subject in need thereof of, with a therapeutically effective amount of a fructopyranose sulfamate and erythropoietin, wherein the amount of the fructopyranose sulfamate and the amount of the erythropoietin are selected to produce a synergistic effect.

The invention further includes a method of improving memory and/or mental capacity and/or of halting the progression of mental deterioration, which method comprises co-therapy, to subject in need thereof of, with a therapeutically effective amount of fructopyranose sulfamate and erythropoietin, wherein the amount of the fructopyranose sulfamate and the amount of the erythropoietin are selected to produce a synergistic effect.

The invention further includes a method of improving memory and/or mental capacity and/or of halting the progression of mental deterioration, including, but not limited to, in an Alzheimer's disease patient, which method comprises co-therapy, to subject in need thereof of, with a therapeutically effective amount of fructopyranose sulfamate and erythropoietin, wherein the amount of the fructopyranose sulfamate and the amount of the erythropoietin are selected to produce a synergistic effect.

The invention also includes a method of treating and/or preventing the neurological and psychiatric manifestations resulting from acute neurodegenerative disorders (including, but not limited to, depression, anxiety disorders, psychopathology, cognitive deficits, memory loss and diminished mental capacity), which method comprises co-therapy, to a subject in need thereof, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing the neurological (including, but not limited to, cognitive) and psychiatric (including, but not limited to, psychopathology, depression, or anxiety), manifestations associated with chronic neurodegenerative disorders, which method comprises co-therapy, to a subject in need thereof of, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing the neurological and psychiatric manifestations resulting from disease or injury of any physiological system, which method comprises co-therapy, to a subject in need thereof, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing the neurological and psychiatric manifestations of a peripheral disease, which method comprises co-therapy, to a subject in need thereof, with a therapeutically effective amount of a fructopyranose sulfamate and erythropoietin, wherein the amount of the fructopyranose sulfamate and the amount of the erythropoietin are selected to produce a synergistic effect.

The invention also includes a method of treating and/or preventing the neurological and psychiatric manifestations resulting from an epileptic condition, including the neurological and psychiatric manifestations resulting from post-seizure or post-ictal states (such as psychosis, depression, anxiety disorders, cognitive deficits, memory loss) and the neurological and psychiatric manifestations that occur interictally (including, but not limited to, psychosis), which method comprises co-therapy, to a subject in need thereof, with a therapeutically effective amount of a fructopyranose sulfamate and erythropoietin, wherein the amount of the fructopyranose sulfamate and the amount of the erythropoietin are selected to produce a synergistic effect.

These as well as other embodiments of the present invention will be readily apparent to one of ordinary skill in the art, and are intended to be included within the methods and compositions of the present invention.

As used herein, unless otherwise noted, the term "fructopyranose sulfamate" shall mean a compound of the formula I:

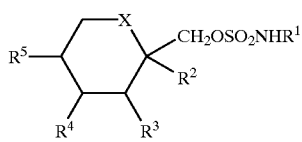

I wherein:
  X is $CH_2$ or oxygen;
  $R_1$ is hydrogen or alkyl; and
  $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula II:

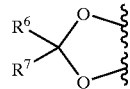

II wherein:
  $R_6$ and $R_7$ are the same or different and are hydrogen, lower alkyl or are alkyl and are joined to form a cyclopentyl or cyclohexyl ring.

$R_1$ in particular is hydrogen or alkyl of about one to four carbons, such as methyl, ethyl and isopropyl. Alkyl throughout this specification includes straight and branched chain alkyl. Alkyl groups for $R_2$, $R_3$, $R_4$, $R_5$, $R_6$ and $R_7$ are of about one to three carbons and include methyl, ethyl, isopropyl and n-propyl. When X is $CH_2$, $R_4$ and $R_5$ may combine to form a benzene ring fused to the 6-membered X-containing ring, i.e., $R_4$ and $R_5$ are defined by the alkatrienyl group $=C-CH=CH-CH=$.

A particular group of compounds of formula I is that wherein X is oxygen and both $R_2$ and $R_3$ and $R_4$ and $R_5$ together are methylenedioxy groups of the formula II, wherein $R_6$ and $R_7$ are both hydrogen, both alkyl, or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula I, is that wherein both $R_2$ and $R_3$ are hydrogen.

The fructopyranose sulfamates, compounds of formula I, may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium t-butoxide or sodium hydride at a temperature of about $-20°$ to $25°$ C. and in a solvent such as toluene, THF, or dimethylformamide wherein R is a moiety of the following formula III:

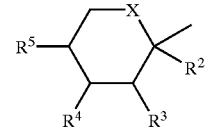

III (b) Reaction of an alcohol of the formula $RCH_2OH$ with sulfurylchloride of the formula $SO_2Cl_2$ in the presence of a base such as triethylamine or pyridine at a temperature of about $-40°$ to $25°$ C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of about $40°$ to $25°$ C. in a solvent such as methylene chloride or acetonitrile to produce a compound of formula I. The reaction conditions for (b) are also described by T. Tsuchiya et al., *Tetrahedron Letters* (1978) vol. 3365.

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah, *Tetrahedron Letters* (1975), vol. 2455. The azidosulfate is then reduced to a compound of formula I wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R^2$ and $R^3$, and $R^4$ and $R^5$ are identical and are of the formula II may be obtained by the method of R. F. Brady, *Carbohydr. Res.* (1970) 14:35 or by reaction of the trimethylsilyl enol ether of a $R_6COR_7$ ketone or aldehyde with fructose at a temperature of about 25° C., in a solvent such a halocarbon, e.g. methylene chloride, in the presence of a protic acid such as hydrochloric acid or a Lewis Acid such as zinc chloride. The trimethylsilyl enol ether reaction is described by Larson et al., *J. Org. Chem.* (1973) 38:3935.

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in *Modern Synthetic Reactions* (2nd Ed.) pages 45 to 144 (1972).

The fructopyranose sulfamates, compounds of formula I, may also be made by the process disclosed in U.S. Patents: U.S. Pat. No. 4,513,006, U.S. Pat. No. 5,242,942, and U.S. Pat. No. 5,384,327, which are incorporated by reference herein.

The fructopyranose sulfamates, compounds of formula I, include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygen of the methylenedioxy group of formula II are attached on the same side of the 6-membered ring.

As used herein, unless otherwise noted, the term "Erythropoietin or EPO" shall include those polypeptides and proteins that have the biological activity of human erythropoietin, as well as erythropoietin analogs, erythropoietin isoforms, erythropoietin mimetics, erythropoietin fragments, erythropoietin receptor or signal transducing activating peptide sequences (including, but not limited to, the 17 amino acid peptide sequence of EPO disclosed by O'Brien et al., in U.S. Pat. No. 5,700,909 and the peptide dimers that bind to the erythropoietin receptor and simulate its function, as disclosed by Zivin et al., in WIPO publication WO 96/40772), hybrid erythropoietin proteins, erythropoietin receptor activating antibodies and fragments thereof such as those disclosed in U.S. Pat. Nos. 5,885,574, and 6,319,499, fusion proteins oligomers and multimers of the above, homologues of the above, glycosylation pattern variants of the above (including de-glycosylated and hyperglycosylated variants of the above), and muteins of the above, regardless of the biological activity of same, and further regardless of the method of synthesis or manufacture thereof, including, but not limited to, recombinant whether produced from cDNA or genomic DNA, synthetic, transgenic, and gene activated methods. Specific examples of erythropoietin include, Epoetin alfa (EPREX®, ERYPO®, PROCRIT®), novel erythropoiesis stimulating protein (NESP, ARANESPO®) (a hyperglycosylated analog of recombinant human erythropoietin described in European patent application EP 640619), darbepoetin-alfa, (ARANESP®), human erythropoietin analog—human serum albumin fusion proteins described in WIPO publication WO 99/66054, erythropoietin mutants described in WIPO publication WO 99/38890, erythropoietin omega, which may be produced from an Apa I restriction fragment of the human erythropoietin gene described in U.S. Pat. No. 5,688,679, altered glycosylated human erythropoietin described in WIPO publication WO 99/11781, PEG conjugated erythropoietin analogs, including, but not limited to, those described in WIPO publication WO 98/05363 or U.S. Pat. No. 5,643,575. Specific examples of cell lines modified for expression of endogenous human erythropoietin are described in WIPO publications WO 99/05268 and WO 94/12650. The generally preferred form of EPO is purified, recombinant human EPO (rhEPO), distributed under the trademarks of EPREX®, ERYPO®, or PROCRIT®. Another preferred form of EPO is darbepoetin-alfa, distributed under the trademark ARANESP®.

As used herein, the term "subject", refers to an animal, preferably a mammal, most preferably a human, who is the object of treatment, observation or experiment.

As used herein, the term "composition" is intended to encompass a product comprising the specified ingredients in the specified amounts, as well as any product which results, directly or indirectly, from combinations of the specified ingredients in the specified amounts.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy comprising administration of one or more fructopyranose sulfamates and erythropoietin, "therapeutically effective amount" shall mean that amount of the combination of agents taken together so that the combined effect elicits the desired biological or medicinal response. For example, the therapeutically effective amount of co-therapy comprising administration of a fructopyranose sulfamate and erythropoietin would be the amount of the fructopyranose sulfamate and the amount of the erythropoietin that when taken together or sequentially have a combined effect that is therapeutically effective. Further, it will be recognized by one skilled in the art that in the case of co-therapy with a therapeutically effective amount, as in the example above, the amount of the fructopyranose sulfamate and/or the amount of the erythropoietin individually may or may not be therapeutically effective.

Wherein the present invention is directed to the administration of co-therapy, the compounds may be co-administered simultaneously, sequentially, separately or in a single pharmaceutical composition. Where the compounds are administered separately, the number of dosages of each compound given per day, may not necessarily be the same, e.g. where one compound may have a greater duration of activity, and will therefore, be administered less frequently. Further, where the compounds are administered separately, the dosage forms of administration of each compound, may not necessarily be the same, e.g. where one compound may be administered in a solid, oral form and another may be administered intravenously or subcutaneously.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

For pharmaceutical administration, EPO may be administered by any suitable means, as would be apparent to one skilled in the art. As used for administration of EPO, the phrase "therapeutically effective" is from about 1 to 15000 I.U./kg or 1 to 10000 I.U./kg, or 1 to 5000 I.U./kg body weight, using any dosing regimen that provides a therapeutical effect. EPO may be administered by any parenteral method, including, but not limited to oral, pulmonary, intraperitoneal (ip), intravenous (iv), intramuscular (im), subcutaneous (sc), transdermal, buccal, nasal sublingual, ocular, rectal and vaginal. EPO may also be administrated directly to the nervous system including, but not limited to intracerebral, intraventricular, intracerebroventricular, intrathecal, intracisternal, intraspinal and/or peri-spinal routes of administration by delivery via intracranial or intravertebral needles and/or catheters with or without pump devices. It will be readily apparent to those skilled in the art that any EPO dose or frequency of EPO administration that provides the therapeutic effect described herein is suitable for use in the present invention.

For pharmaceutical administration, topiramate may be administered by any suitable means, as would be apparent to one skilled in the art. As used for administration of topiramate, the phrase "therapeutically effective" is from about 10 to 1000 mg total dose (for 70 kg individual), preferably from about 10 to 640 mg total dose, more preferably from about 25 to 400 mg total dose or from about 50 to 300 mg total dose, using any dosing regimen that provides a therapeutical effect. Topiramate may be administered by any parenteral method, including, but not limited to oral, pulmonary, intraperitoneal (ip), intravenous (iv), intramuscular (im), subcutaneous (sc), transdermal, buccal, nasal, sublingual, ocular, rectal and vaginal. Topiramate may also be administrated directly to the nervous system including, but not limited to intracerebral, intraventricular, intracerebroventricular, intrathecal, intracisternal, intraspinal and/or peri-spinal routes of administration by delivery via intracranial or intravertebral needles and/or catheters with or without pump devices. It will be readily apparent to those skilled in the art that any topiramate dose or frequency of topiramate administration that provides the therapeutic effect described herein is suitable for use in the present invention.

The neurite outgrowth assays described herein are disclosed in the art as predictive of enhancement of maintenance and recovery of neural cells and neural function, by promoting recovery of synaptic contacts and connections, and by stabilizing the neuronal and neural circuitries, and are thus predictive of a test compound's ability to affect a neurodegenerative disorder, whether acute or chronic. (C. S. von Bartheld, *Histol. Histopathol.* (1998) 13:437–459; H. Rauvala and H. B. Peng, *Prog. Neurobiol.* (1997) 52:127–144; Ronn et al., *Int. J. Dev. Neurosci.* (2000) 18:193–199; M. E. Schwab, *Curr. Opin. Neurol. Neurosurg.* (1993) 6:549–553; I. Mocchetti and J. R. Wrathall, *J. Neurotrauma.* (1995) 12:853–870; A. M. Davies, *Curr. Biol.* (2000) 10:R198–200; Verderio et al., *Cell. Mol. Life Sci.* (1999) 55:1448–1462; I. Semkova and J. Krieglstein J, *Brain Res. Brain Res. Rev.* (1999) 30:176–188). Additional models which are known to be predictive of efficacy in neurodegenerative disorders include, but are not limited to, models of stroke, brain and spinal cord trauma/injury (Zhang et al., *Brain Res.* (1999) 842:211–214; Sadamoto et al., *Biochem. Biophys. Res. Commun*, (1998) 253:26–32; W. M. Armstead, *Microcirculation* (2000) 7:225–235; B. H. Han and D. M. Holtzman, *J. Neurosci.* (2000) 20:5775–5781; Di Giulio et al., *Int. J. Dev. Neurosci.* (2000) 18:339–346; Y. Taoka and K. Okajima, *Prog. Neurobiol.* (1998) 56:341–358; D. M. Basso, *Phys. Ther.* (2000) 80:808–817; Brines et al., *P.N.A.S. USA* (2000) 97:10526–10531; Raghupathi et al., *J. Neurotrauma.* (2000) 17:927–938; and H. L. Laurer and T. K. McIntosh, *Curr. Opin. Neurol.* (1999) 12:715–721).

We now describe results of the effectiveness of topiramate, rhEPO and the combination thereof, on neurite outgrowth on hippocampal and cortical cells. Each set of assay results represents a separate data set, wherein the data is presented as a % change relative to an internal control. Negative values are not interpreted as deleterious effects, rather, values of −1 to −2 are not different from the internal control. The instance of a measured value of −14 occurred only once, in an isolated case.

As used herein, the term "synergy" or "synergistic effect" when used in connection with a description of the efficacy of a combination of agents, shall mean any measured effect of the combination which is greater than the value predicted from a sum of the effects of the individual agents. (Greco et al., *Pharmacol. Rev.* (1995) 47:331–385).

The following Examples are set forth to aid in the understanding of the invention, and are not intended and should not be construed to limit in any way the invention set forth in the claims which follow thereafter.

EXAMPLE 1

Neurite Outgrowth Effects on Hippocampal and Cortical Cells

Cell Culture

Dissociated hippocampal and cortical cell cultures were established from embryonic Day 18 rat fetuses as previously described (Mattson et al., 1994). Briefly, fetuses were removed via cesarean section from pregnant rats (Sprague-Dawley) and anesthetized with halothane according to the AVMA Panel on Euthanasia. Fetuses were decapitated and the brains were removed and placed in HEPES-buffered Hank's Balanced Salt solution (HBSS; Gibco). The hippocampi and cortices were dissected out and pooled according to tissue-type. Tissue was trypsinized for fifteen minutes (1 mg/ml trypsin-HBSS; Worthington), rinsed with fresh HBSS, incubated in trypsin inhibitor (1 mg/ml; Sigma) for five minutes, rinsed again with fresh HBSS and then triturated in 1 ml fresh HBSS with a fire-polished glass pipette. Dissociated cells were seeded at 20,000 cells (Array Scan Assay) and 30,000 cells (MAP2-FITC assay)/well onto poly-D-lysine coated 96-well plates (Collaborative BioScience). Each well contained 100 μl of Eagle's Minimal Essential Media (MEM; Gibco) supplemented with 26 mM NaHCO$_3$ (Sigma), 56 mM glucose (Sigma), 15 mM KCl (Sigma), 1 mM sodium pyruvate (Sigma), 1.1 mM L-glutamine (Sigma), 10% (v/v) heat-inactivated fetal bovine serum (Hyclone), and 0.001% gentamicin sulfate (Sigma) (pH 7.4). Cells were allowed to attach for twenty-four hours in a humidified 37° C. 5% CO$_2$ incubator before experimental treatment. The culture media was aspirated and exchanged with fresh media every three days.

Neurite Outgrowth Array Scan Measurement

Twenty-four hours after plating, rat cerebral cortical cell cultures, prepared as described above, were treated with vehicle (phosphate buffered saline+0.1% bovine serum albumin; Sigma), topiramate, EPO (rhEPO; 50 μM stock in 0.2 M citrate, 0.585 g/L NaCl diluted to appropriate concentrations in phosphate buffered saline+0.1% bovine serum albumin (BSA; Sigma)) or a combination of topiramate and EPO. On the third day in culture, the media was aspirated off and replaced with fresh media and test compound.

Culture media (prepared as described above) was aspirated and replaced with formaldehyde/Hoechst solution (fix cells and stain nuclei). Cultures were incubated in this solution for twenty minutes, then washed with permeabilization/wash/antibody (PWA) buffer. The buffer solution was aspirated and 100 μl of primary antibody (rabbit polyclonal IgG; specific for an epitope present only in neurons and neurites) was added to each well. The cultures were incubated for 60 minutes, then washed with PWA buffer. The buffer solution was again aspirated and 100 μl of secondary antibody (Alexa Fluor 488 conjugated goat anti-rabbit IgG) was added to each well. The cultures were incubated for 60 minutes and then washed with PWA buffer, followed by phosphate buffered saline (PBS) solution.

100 μl PBS-CM were added to each well, the plates were sealed and fluorescence was read on the Array Scan II System. (All reagents for this measurement were provided by the neurite outgrowth hit kit # K07-0001-1, Cellomics Inc.) The Array Scan algorithm for neurite outgrowth calculates the neurite outgrowth index for each field per well. This number represents the number of neurons with neurites divided by the total number of neurons in the field.

The ability of rhEPO, topiramate (TPM) and the combination of rhEPO and topiramate to increase neurite outgrowth in rat cortical cell cultures was determined according to the procedure described above, with results as listed in Table 1. For each dosage concentration, the measured value in the Table represents the mean percent change of eight experimental observations (from vehicle control). The abbreviation NT, as used in the Table below represents a concentration not tested.

TABLE 1

Array Scan Assay, Neurite Outgrowth (Neuron-specific) in Rat Cortical Cultures

| Concentration | rhEPO | Topiramate | rhEPO + 1 pM TPM (Predicted) | rhEPO + 1 pM TPM (Measured) | rhEPO + 100 pM TPM (Predicted) | rhEPO + 100 pM TPM (Measured) |
|---|---|---|---|---|---|---|
| 1 fM | 29 | NT | 29 | 40(*) | 41 | 13 |
| 10 fM | −1 | NT | −1 | 21(*) | 11 | 15(*) |
| 100 fM | 28 | 4 | 28 | 16 | 40 | 15 |
| 1 pM | 9 | 0 | 9 | 27(*) | 21 | 21 |
| 10 pM | 11 | 20 | 11 | 23(*) | 23 | 14 |
| 100 pM | | 12 | | | | |

The measured results show greater than additive neurite outgrowth promotion for cell cultures treated with both topiramate and rhEPO. That is, these concentrations induced a synergistic effect (*), more than the predictive sum of the individual effects, on neurite outgrowth of cortical neurons.

EXAMPLE 2

Neurite Outgrowth MAP2-FITC Assay for Rat Hippocampal Cells

Twenty-four hours after plating, rat hippocampal cell cultures, prepared as in Example 1, were treated with vehicle (phosphate buffered saline+0.1% bovine serum albumin; Sigma), topiramate, EPO (rhEPO; 50 μM stock in 0.2 M citrate, 0.585 g/L NaCl diluted to appropriate concentrations in phosphate buffered saline+0.1% bovine serum albumin (BSA; Sigma)) or a combination of topiramate and EPO. On the third day in culture, the media was aspirated off and replaced with fresh media and test compound. At one week in culture, the cells were fixed with 10% phosphate-buffered formalin for fifteen minutes, then rinsed with phosphate buffered saline and placed in blocking serum for thirty minutes (horse serum; 1:50 dilution in phosphate buffered saline; Vector Labs). Cultures were rinsed again with phosphate buffered saline and then incubated in primary antibody for two hours (microtubule-associated protein-2 (MAP-2) is a selective marker for dendritic processes; anti-mouse monoclonal (Chemicon); 1:1000 dilution of MAP-2 in antibody diluent (Zymed)). Negative control wells were incubated in antibody diluent alone. Background signal was determined by blank wells (cell-free) incubated with or without antibody. Cultures were rinsed again with phosphate buffered saline and then placed in fluorescein-labeled secondary antibody for 1 hr (FITC; anti-mouse IgG; rat adsorbed; 1:50 dilution in DPBS; Vector Labs). Cultures were rinsed a final time with phosphate buffered saline. The plates were then read on a Cytofluor 4000 fluorescence plate reader. Neurite outgrowth was expressed as percent change from control (vehicle; mean fluorescence±SEM).

The ability of rhEPO, topiramate and the combination of rhEPO and topiramate to increase neurite outgrowth in rat hippocampal cultures was determined according to the procedure described above, with results as listed in Table 2. For each case or treatment, the measured value in the Table represents the mean percent change of eight experimental observations (from vehicle control). The abbreviation NT, as used in Table 2 represents a concentration not tested.

determined by blank wells (cell-free) incubated with or without antibody. Cultures were rinsed again with phosphate

TABLE 2

Neurite Outgrowth in Rat Hippocampal Cultures

| Concentration | rhEPO | Topiramate | rhEPO + 1 pM TPM (Predicted) | rhEPO + 1 pM TPM (Measured) | rhEPO + 100 pM TPM (Predicted) | rhEPO + 100 pM TPM (Measured) |
|---|---|---|---|---|---|---|
| 1 fM | 21 | NT | 35 | 37(*) | 12 | 30(*) |
| 10 fM | 15 | NT | 29 | 40(*) | 6 | 29(*) |
| 100 fM | 12 | 33 | 26 | 38(*) | 3 | 31(*) |
| 1 pM | 20 | 14 | 34 | 32 | 11 | 20(*) |
| 10 pM | 21 | 5 | 35 | 12 | 12 | 13 |
| 100 pM | | −9 | | | | |

The results listed above show that hippocampal neurons treated with both rhEPO and topiramate, at various concentrations, resulted in a significant increase in neurite outgrowth. The data showed that the neurite outgrowth promoting effect was stronger when both rhEPO and topiramate were administered, at several specific concentrations, when compared with the neurite outgrowth promoting effect of rhEPO and topiramate tested separately. That is, a synergistic outgrowth response (*) in hippocampal neurons was obtained when the cell cultures were treated with both topiramate and erythropoietin and this synergistic response was greater than the effect that would be predicted from the sum of the responses to individual treatments.

EXAMPLE 3

Neurite Outgrowth MAP2-FITC Assay for Rat Cortical Cells

Twenty-four hours after plating, rat cortical cell cultures, prepared as in Example 1, were treated with vehicle (phosphate buffered saline+0.1% bovine serum albumin; Sigma), topiramate, EPO (rhEPO; 50 μM stock in 0.2 M citrate, 0.585 g/L NaCl diluted to appropriate concentrations in phosphate buffered saline+0.1% bovine serum albumin (BSA; Sigma)) or a combination of topiramate and EPO. On the third day in culture, the media was aspirated off and replaced with fresh media and test compound. At one week in culture, the cells were fixed with 10% phosphate-buffered formalin for fifteen minutes, then rinsed with phosphate buffered saline and placed in blocking serum for thirty minutes (horse serum; 1:50 dilution in phosphate buffered saline; Vector Labs). Cultures were rinsed again with phosphate buffered saline and then incubated in primary antibody for two hours (microtubule-associated protein-2 (MAP-2) is a selective marker for dendritic processes; anti-mouse monoclonal (Chemicon); 1:1000 dilution of MAP-2 in antibody diluent (Zymed)). Negative control wells were incubated in antibody diluent alone. Background signal was determined by blank wells (cell-free) incubated with or without antibody. Cultures were rinsed again with phosphate buffered saline and then placed in fluorescein-labeled secondary antibody for one hour (FITC; anti-mouse IgG; rat adsorbed; 1:50 dilution in DPBS; Vector Labs). Cultures were rinsed a final time with phosphate buffered saline. The plates were then read on a Cytofluor 4000 fluorescence plate reader. Neurite outgrowth was expressed as percent change from control (vehicle; mean fluorescence±SEM).

The ability of rhEPO, topiramate and the combination of rhEPO and topiramate to increase neurite outgrowth in rat cortical cultures was determined according to the procedure described above, with results as listed in Table 3. For each case or treatment, the measured value in the Table represents the mean percent change of eight experimental observations (from vehicle control). The abbreviation NT, as used in Table 3 represents a concentration not tested.

TABLE 3

Neurite Outgrowth in Rat Cortical Cultures

| Concentration | rhEPO | Topiramate | rhEPO + 1 pM TPM (Predicted) | rhEPO + 1 pM TPM (Measured) | rhEPO + 100 pM TPM (Predicted) | rhEPO + 100 pM TPM (Measured) |
|---|---|---|---|---|---|---|
| 1 fM | −14 | NT | 9 | 20(*) | 23 | 34(*) |
| 10 fM | −2 | NT | 21 | 33(*) | 35 | 47(*) |
| 100 fM | 10 | 24 | 33 | 21 | 47 | 34 |
| 1 pM | 19 | 23 | 42 | 23 | 56 | 20 |
| 10 pM | 24 | 30 | 47 | 29 | 61 | 17 |
| 100 pM | | 37 | | | | |

The results listed above show that cortical neurons treated with both rhEPO and topiramate, at various concentrations, resulted in a significant increase in neurite outgrowth. The data showed that the neurite outgrowth promoting effect was stronger when both rhEPO and topiramate were administered, at several specific concentrations, when compared with the neurite outgrowth promoting effect of rhEPO and topiramate tested separately. That is, a synergistic outgrowth response (*) in cortical neurons was obtained for treatment of the cell cultures with both rhEPO and topiramate, and this synergistic response was greater than the effect that would be predicted from the sum of the responses to individual treatments.

The synergistic neurite promoting effect observed in each of the above assays, when both rhEPO and topiramate were dosed on the same cell culture, is expected to result in increased benefit to the maintenance and recovery of neural cells by promoting re-establishment of synaptic contacts and connections, and by stabilizing neuronal and neural circuitries. This translates into an expected benefit for the underlying pathophysiology of neurological dysfunctions which are associated with the loss of synaptic contacts and connections and marked disruption of neuronal and neural circuitries.

Thus, for treating a neurological dysfunction, one or more fructopyranose sulfamates may be administered as co-therapy with erythropoietin, wherein the amount of the fructopyranose sulfamate(s) and the amount of the erythropoietin are selected to produce a synergistic effect. More particularly, the fructopyranose sulfamate is administered at a dosage in the range of about 10 to 1000 mg, and the erythropoietin is administered at a dosage in the range of about 1 to 15000 I.U./kg, or about 1 to 10000 I.U./kg or about 1 to 15000 I.U./kg, body weight.

To prepare the pharmaceutical compositions of the present invention, one or more fructopyranose sulfamates, EPO or a combination thereof, are intimately admixed with a pharmaceutically acceptable carrier according to conventional pharmaceutical compounding techniques, wherein the carrier may take a wide variety of forms depending on the form of the preparation desired for administration, e.g. i.v. sterile injectable formulations will be prepared using appropriate solubilizing agents.

Preferably the pharmaceutical composition(s) are in unit dosage forms such as tablets, pills, caplets, capsules (each including immediate release, timed release and sustained release formulations), powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions such as tablets, the principal active ingredient(s) are mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing a suitable amount of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

For oral administration in the form of a tablet or capsule, the active drug component(s) may be combined with an oral, non-toxic pharmaceutically acceptable inert carrier such as ethanol, glycerol, water and the like. Moreover, when desired or necessary, suitable binders, lubricants, suspending agents, disintegrating agents, coloring agents, flavorants, sweeteners, preservatives, dyes, coatings and other inert pharmaceutical excipients can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing liquid formulations, for administration orally or by injection, the principal active ingredient(s) is mixed with a pharmaceutical carrier, e.g. aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. Forms useful for parenteral administration include sterile solutions, emulsions and suspensions. Isotonic preparations which generally contain suitable preservatives are employed when intravenous administration is desired.

Furthermore, the active drug component(s) may alternatively be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

The active drug component(s) may be administered via stable formulations for pulmonary administration, for example, as disclosed by Colin et al., in U.S. Pat. No. 5,354,934 (WIPO publication WO 95/03034). The active drug component(s) may also be administered in the form of a spray dried formulation, for example, as disclosed by Mehta et al., in U.S. Pat. No. 6,001,800, issued Dec. 14, 1999.

The active drug component(s) may be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

The active drug component(s) may also be delivered by the use of monoclonal antibodies as individual carriers to which the compound molecules are coupled. The active drug component(s) may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, active drug component(s) may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for promoting neurite outgrowth in a subject, comprising administering an amount of topiramate and erythropoietin effective to promote the neurite outgrowth; wherein the amount of topiramate and the amount of erythropoietin are selected to produce a synergistic effect.

2. The method of claim 1, wherein the amount of topiramate is from about 10 to 1000 mg.

3. The method of claim 1, wherein the erythropoietin is epoetin alfa.

4. The method of claim 1, wherein the amount of erythropoietin is from about 1 to 15000 I.U./kg.

5. The method of claim 1, wherein said subject has epilepsy.

6. A pharmaceutical composition comprising topiramate, erythropoietin and a pharmaceutically acceptable carrier.

7. A process for making a pharmaceutical composition comprising mixing topiramate, erythropoietin and a pharmaceutically acceptable carrier.

* * * * *